United States Patent [19]

Nailor et al.

[11] Patent Number: 5,100,238
[45] Date of Patent: Mar. 31, 1992

[54] CUVETTE AND APPARATUS FOR PERFORMING BIOLOGICAL ASSAYS

[75] Inventors: Paul R. Nailor, London, England; Ann T. Miller, Cambridge, Great Britain

[73] Assignee: Orion Corporation Limited, Espoo, Finland

[21] Appl. No.: 317,474

[22] PCT Filed: Jun. 13, 1988

[86] PCT No.: PCT/GB88/00457
§ 371 Date: Feb. 8, 1989
§ 102(e) Date: Feb. 8, 1989

[87] PCT Pub. No.: WO88/09925
PCT Pub. Date: Dec. 15, 1988

[30] Foreign Application Priority Data
Jun. 11, 1987 [GB] United Kingdom ............... 8713649

[51] Int. Cl.⁵ .............................................. G01N 21/51
[52] U.S. Cl. ..................................... 356/246; 356/336
[58] Field of Search ............... 356/336, 338, 246, 343; 250/573

[56] References Cited

U.S. PATENT DOCUMENTS

| | | | |
|---|---|---|---|
| 3,512,877 | 5/1970 | Mohr | 356/246 |
| 4,465,938 | 8/1984 | Kato et al. | 356/246 |
| 4,566,791 | 1/1986 | Goldsmith | 356/246 |
| 4,707,131 | 11/1987 | Schiek | 356/338 |
| 4,842,406 | 6/1989 | Van Bargen | 356/336 |

Primary Examiner—Richard A. Rosenberger
Attorney, Agent, or Firm—Lee, Mann, Smith, McWilliams, Sweeney & Ohlson

[57] ABSTRACT

A cuvette adapted to contain spherical particles having a specific binding agent on the surface thereof and which have a detectably different light scattering characteristic in the presence of a material having a specific binding partner thereof, and which includes a window through which light can be projected for the purpose of determining any change in light scattering properties of the contents of the cuvette, and an optical element occupying at least part of a wall of the cuvette which, when light passes therethrough, causes at least some of the light to be deflected off axis towards a particular point. By using such a cuvette in combination with a light level detector located as the said particular point, a cuvette can be identified before an assay is performed by checking the light level at the said particular point. The optical element may be a hologram or a diffraction grating or a lens or any combination thereof. A method of checking whether a cuvette inserted into a testing apparatus, includes such an optical element is described as well as a method of performing an assay which includes a cuvette validating step.

14 Claims, 5 Drawing Sheets

CUVETTE AND APPARATUS FOR PERFORMING BIOLOGICAL ASSAYS

Field of Invention

This invention relates to biological assays of the type in which a cuvette is filled with a material having a specific binding agent on its surface and whose ability to scatter light changes upon the addition of a sample containing a specific binding partner to the surface bound agent. The invention also relates to apparatus by which such assays may be performed, and in particular relates to a device and technique for verifying whether a particular cuvette is appropriate for use in a particular analysing apparatus.

BACKGROUND TO THE INVENTION

Latex agglutination is a well known and established immuno-assay test. The basis for the technique lies in the ability to coat latex spheres (300–800 nm in diameter) with a specific antibody. If the spheres are exposed to a sample containing the relevant antigen then bonding can occur leading to clumping of the latex balls. An alternative form of the test uses latex spheres coated in antigen, samples can then be tested for the presence of the relevant antibody.

Traditionally the test has been carried out manually by transferring quantities of control and test latex from phials within a reagent kit, to a piece of black card, and mixed with the sample to be tested. Agglutination of the latex balls can be clearly seen against the dark background.

It is also known to perform a biological assay by filling a cuvette with a plurality of small diameter spheres (typically of latex) coated with a specific binding agent and to add a sample material to the cuvette and observe whether there is any change in the light scattering properties of the contents of the cuvette as a result of any binding of the sample to the spheres. The change in light scattering properties is brought about by the increased diameter of the spheres due to the binding of the sample material thereto, and if there is binding, then the sample is assumed to contain the specific binding partner of the material on the spheres.

It is one object of the present invention to provide an improved cuvette by which such an assay can be performed.

It is another object of the present invention to provide an improved analyser for performing assays using such cuvettes and which performs a verifying test on a cuvette before a biological assay is performed.

It is a further object of the invention to provide an improved method of performing a biological assay.

SUMMARY OF THE INVENTION

According to one aspect of the invention a cuvette adapted to contain spherical particles having a specific binding agent on the surface thereof and which have a detectably different light scattering characteristic in the presence of a material having a specific binding partner therefor, includes a window through which light can be projected for the purpose of determining any change in light scattering properties of the contents of the cuvette, is characterised by an optical element in or on a wall of the cuvette, which when light passes therethrough, causes at least some of the light to be deflected towards a particular point.

By using such a cuvette in combination with a light level detector located at said particular point, a cuvette can be validated before an assay is performed by checking the light level at the said particular point.

Where the cuvette can only be inserted into a testing apparatus in one way, the point is fixed in space and it is merely necessary to check the light level at the said point and determine whether light is incident thereat.

If the cuvette is rotatable about its axis, the point can lie at any position around a circular path and either the light detector must be moveable around the path to find the particular point, or the cuvette must be rotated to move the point onto the detector.

In manner known per se the cuvette contains small latex spheres which are coated with the specific binding agent and the reagent sample is checked by determining whether there is any change in the pattern of the light scattered from the spheres after the sample reagent has been added. (It is understood that the change in scattered light is brought about by the clumping together of the spheres due to agglutination when the specific binding partner is present in the sample reagent).

The optical element may be in the form of a hologram or a diffraction grating or a lens, in or on a wall of the cuvette, or any combination thereof.

The light sensitive detector may comprise a photocell.

Circuit means may be provided, responsive to the detector output, to provide an electrical pulse when light, focused, or diffracted, or otherwise diverted by the optical element, is incident thereon.

Conveniently, the cuvette is rotatable about its axis and the optical element acts so as to focus or diffract or otherwise divert light parallel to the axis, through the said off-axis point, which as the cuvette is rotated, therefore describes a circular path centered on the axis of the cuvette, and the detector is located at one point around this circular path, and the cuvette is rotated through 360° to produce an electrical pulse in the output of the detector as the diverted light passes through the said point.

Since the cuvette should only produce a single electrical pulse during a 360° rotation, further circuit means may be provided to determine the number of pulses detected, so that a cuvette can be identified reliably and is only indicated as acceptable if only the one pulse is detected during the rotation.

According therefore to another aspect of the invention a method of checking whether a cuvette has a specific optical element includes the steps of illuminating the cuvette and effecting relative rotation between the cuvette and a detector and investigating whether or not the detector generates a particular electrical signal during the rotation, caused by light reflected or refracted or otherwise diverted by the optical element being incident on the detector.

If no such signal is detected, an inhibit signal may be generated preventing further use of the cuvette.

According to another aspect of the present invention, apparatus for performing a biological assay on the contents of a cuvette which contains a plurality of spheres having a specific binding agent on the surface thereof and to which a sample reagent is to be added which may or may not contain a specific binding partner to the material on the spheres, (the presence of a specific binding partner being detected by an increase in diameter of the spheres which results in a different light scatter pattern from the spheres, in the presence of appropriate illumination), and which includes detector means for determining the light scatter pattern before and after a sample reagent has been added, is characterised by:

means for automatically illuminating the cuvette, means for moving same in a predictable manner during at least a preliminary movement of the cuvette, a light sensitive detector for checking for the presence of light at a point along a path along which light will be diverted if the cuvette includes a particular optical element, and circuit means responsive to electrical signals from the light sensitive means which normally inhibits the operation of the apparatus to perform the said assay (or at least inhibit the inspection of the change in light scattering properties of the cuvette contents), but which generates an enabling signal to permit the apparatus to perform the assay if an appropriate signal is generated by the detector means during the said preliminary movement of the cuvette.

The apparatus may include automated sample reagent addition means which likewise may be inhibited until the apparatus has verified that the cuvette incorporates an appropriate optical element.

Alternatively the sample reagent may be added to the cuvette before insertion into the apparatus and the assay is performed after satisfactory verification.

Alternatively the mixing of the sample and the coated spheres may be performed by shaking the cuvette before insertion and/or automatically upon rotation of the cuvette during the preliminary rotation.

The optically based assay may be performed before or during or after the said rotation and only completed (or released as a test result) if an enabling signal is generated during the said rotation.

The optical path within the apparatus may include lenses which co-operate with the optical element if present in the cuvette, to focus light diverted by the optical element, onto the light detector.

Preferably the cuvette is adapted to be rotated about a central axis and drive means is provided within the apparatus for effecting the rotation.

Preferably the verifying step involves a controlled rotation of the cuvette through 360° and the circuit means is rendered sensitive to the output of the light detector to determine any increase in light incident thereon during the controlled rotation of the cuvette.

Since a cuvette which is not validated cannot be used, it is not essential that the verification step is performed before the sample reagent has been mixed with the coated sphere.

According to another aspect of the invention, apparatus for performing a biological assay on a cuvette containing spherical particles by determining changes in light scatter pattern from illumination incident thereon before and after mixing of the particles with a sample reagent, is characterised by:

a plurality of light sensitive detectors mounted to the rear of the cuvette, and means for illuminating the cuvette so as to produce a light scatter pattern for detection by the detector means.

The detectors may be spaced apart in a fixed manner and the array may be moveable so that the actual shape of the light scatter pattern may be determined by, for example, averaging signals obtained from the spaced detectors as they are moved in a predictable and controlled manner relative to the light pattern.

According to another aspect of the invention, an analyser for use with a cuvette which includes an optical element as at least part of one of its walls to divert light incident thereon off-axis in a particular direction, and by which biological assays can be performed by investigating the change in light scatter from coated spheres within the cuvette due to chemical bonding within therewithin the cuvette, comprises:

(a) a source of light for projecting light onto a wall of the cuvette having the optical element formed therein, (b) first light detector means from which electrical signals can be obtained for determining changes in the pattern of the light scattered by particles contained within the cuvette, due to the addition of a sample reagent thereto, and (c) second light detector means radially displaced from the axis for receiving light diverted by an optical element, if present, in the cuvette.

The first light detector means may comprise a pair of detectors, spaced apart, which are moveable towards or away from the cuvette (or the cuvette is moveable relative to the detectors) to provide two electrical signals which can be combined to enable the slope of the light scatter pattern to be derived by computing the mean value of the two signals so obtained.

Validation of a cuvette may be performed by positioning the cuvette so that light incident on the optical element (if present) will be diverted onto the second off-axis detector.

According to another aspect of the invention a method of performing a biological assay comprises the steps of:

(a) inserting a cuvette into an analyser;

(b) shining light through the cuvette so as to be at least in part diverted by an optical element (if one is incorporated within the cuvette);

(c) rotating the cuvette relative to a light detector situated on a circular path which the said diverted light will describe as the cuvette is rotated if the optical element is present, so as to generate an electrical signal if light falls on the detector during the said rotation;

(d) determining if a single electrical pulse appears in the output of the detector during the rotation of the cuvette about its axis thereby to generate an enabling signal;

(e) causing a mixing of the sample reagent and the coated spheres in the cuvette, and (f) performing the assay by comparing light scatter before and after mixing, only if an enabling signal is generated.

The optical element may comprise a holographic lens having a refractive property similar to that of a convex lens.

The light employed to illuminate the cuvette is preferably collimated or at least has well defined convergence.

The detector for detecting the light scatter may be a large area array photodetector or an array of individual photodetectors or a television camera.

The invention may be employed to inhibit the use of cuvettes from an unauthorized source with a particular analyser by arranging that if verification is not obtained, the analyser rejects the cuvette and/or terminates or inhibits the detection steps of the assay forthwith, or simply fails to record the result of the assay.

The cuvette may be a two chamber cuvette containing test and control latex in the two separate chambers. To use such an instrument the operator will first add the sample material to the cuvette containing both test and control latex. The cuvette will then be placed in the instrument which will monitor the rate of agglutination of the particles in the two chambers by measuring the intensity of scattered light as a function of time. The instrument may be a small desk top unit providing an indication of pass/fail or "test again" or in uncertain tests an indication to "dilute the sample". Power to the instrument is typically supplied from internal cells which can be recharged from a standard charging unit.

The cuvette may include a base and a cap which latter contains two ski-slope pockets which contain the dried latex and which prevent its wetting until the cuvette is inverted. The chamber shape and size can help control the size of the mixing bubble and allow it to move smoothly around the chamber.

Preferably a location feature is provided to contol the relative orientation of cap and base ±/-6°, allowing a minimum vent area of 0.2 mm² during closure of the cuvette. This prevents aerosol formation and is closed once assembly of the cap and base has been completed.

Visual guide features may be added to the location feature, to make it easier to orientate by eye.

Where the optical element is a grating this can provide the off-axis verification illumination and the timing signal for optical inspection of the reaction. Typically two gratings are provided 4 mm in diameter and positioned on the external face, concentrically with two 4 mm diameter viewing windows. The gratings may be orientated radialy on the side of the chamber containing the control latex and tangentially on the side containing the test latex in the reaction chamber, thus allowing the instrument to distinguish between light from the control and reaction chambers.

The exact positioning of the gratings relative to the reagent chambers is a matter of choice. Thus in one type of cuvette the gratings may superimpose the viewing windows and the instrument measures the state of the reaction through the viewing windows and the gratings. In another type of cuvette the gratings may be positioned over the regions between the chambers so that the state of reaction can be viewed uninterruptedly through the windows.

A time delay may be introduced into the operation of the instrument to permit inspection of the reaction after the passage of the grating. It should be noted that this should reduce somewhat the instrument tolerance of errors in cuvette filling or of sample foaming.

The gratings typically have a nominal groove spacing of 2.33 u which produce a deflection angle of 25°. The optimum 0.25 u nominal grating depth gives a nominal design diffraction efficiency for the grating of 14% at 940 mm.

There may be loss of diffraction efficiency with moulded gratings but diffraction efficiencies of greater then approximately 5% have been found to give acceptable grating signals from an agglutinating sample in the instrument.

To achieve acceptable bubble mobility cuvettes may be plasma etched in batches, and may be treated with oxygen plasma for a period of time (typically 3 minutes) per batch.

Within 2 days of this treatment the cuvettes are preferably dipped for 30 seconds in a 0.05% Calsoline oil (HS) solution, spun dry and then vacuum dried. As plasma etching does not in general produce a permanent improvement in wettability this secondary process may be necessary to perserve the plasma etched wettability.

Following surface treatment of the cuvettes, the caps may be orientated using a bowl feeder before the control and reagent latexes are deposited into the latex chambers and dried. An asymetric feature may be added to the rim of the cap to assist in orientation for this production operation.

Caps and bases may be packed in vacuum formed trays to maintain appropriate humidity levels in storage and to form a secondary spillage tray for the user when assembling the cuvettes.

The invention envisages that a user will probably purchase the cuvettes in the form of a kit of, say, 20 tests. Each kit might contain a number of individually packed cuvettes, an instruction leaflet, buffer solution (if appropriate) and perhaps a patient record card.

A typical test procedure might be as follows:
prepare patient sample as appropriate.
perform dilution series (if required),
open cuvette packaging,
dispense the instructed quantity of sample into each side of the cuvette using a finn pipette or dropper bottle,
place the lid on the cuvette in approximately the correct orientation,
repeat for other members of the dilution series (if required),
snap the lid shut on the cuvette,
shake the cuvette and place immediately into the instrument (within typically 30 seconds),
shut the instrument lid and wait for the test result,
open the instrument lid to eject the agglutinated cuvette and insert the next,
record result on the patient record card,
dispose of used cuvette.

The invention will now be described by way of example with reference to the accompanying drawings which illustrate apparatus and a modified cuvette constructed in accordance with the invention, and in which.

DESCRIPTION OF THE DRAWINGS

Figure 1:
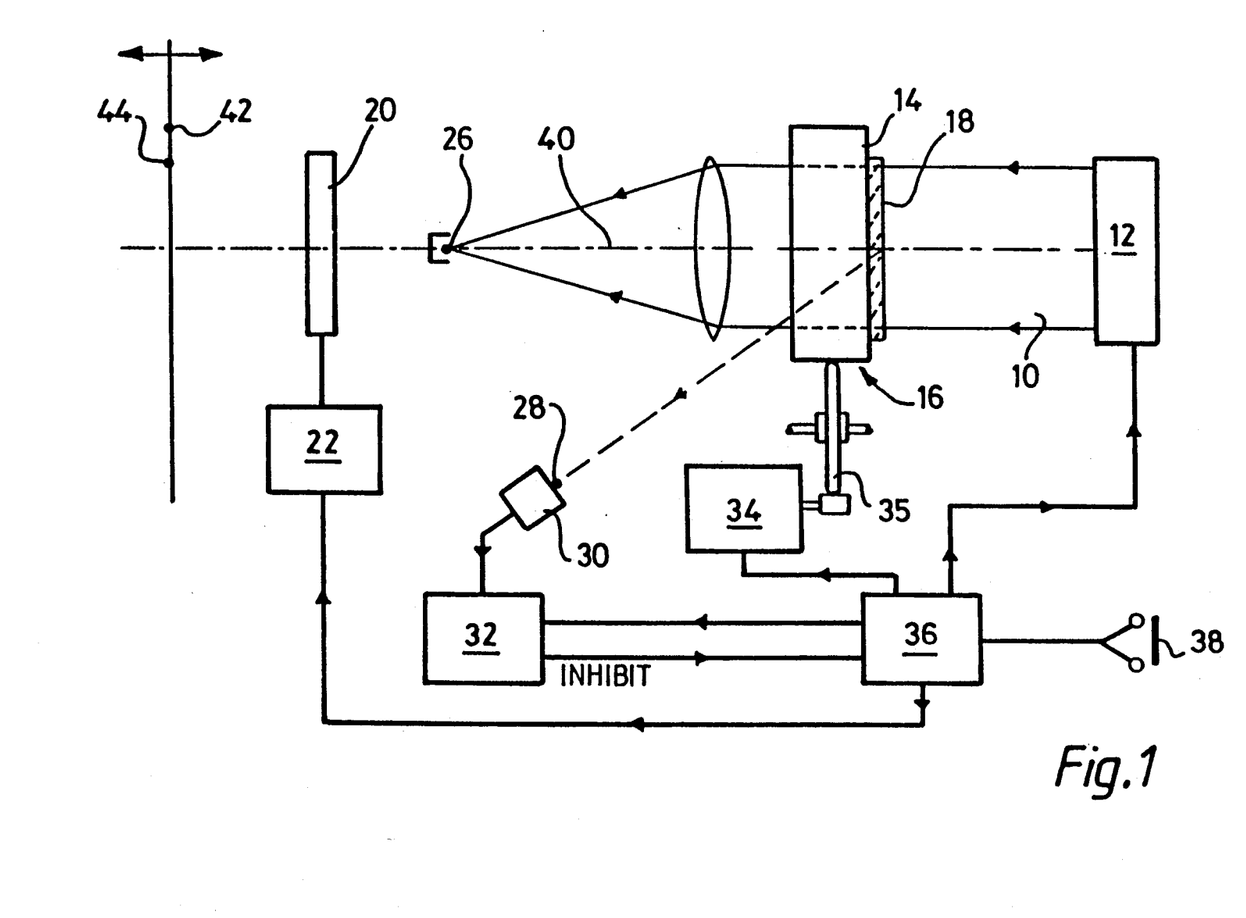
FIG. 1 is a schematic diagram of a modified cuvette and assay apparatus.
Figure 2:
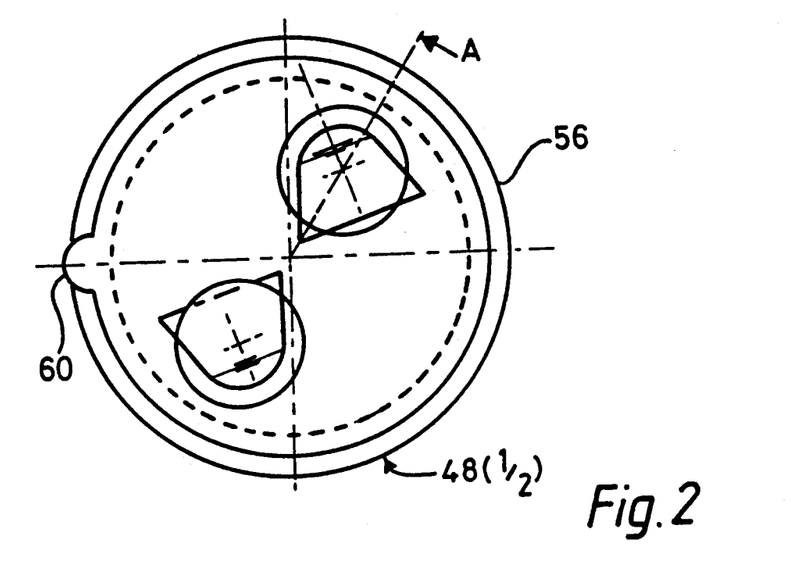
FIG. 2 is a plan view of the cap of a two part cuvette, embodying the invention.
Figure 3:
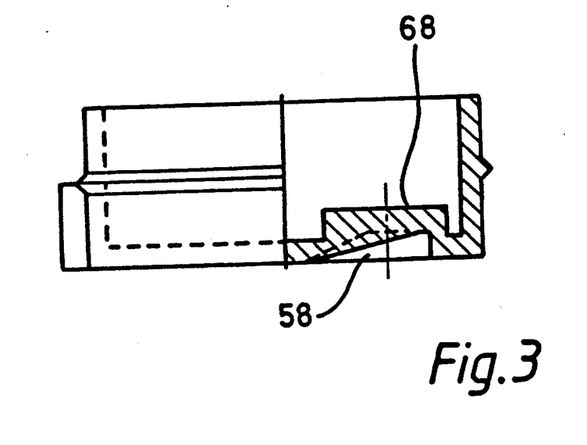
FIG. 3 is a section on the line AA of FIG. 2.
Figure 4:
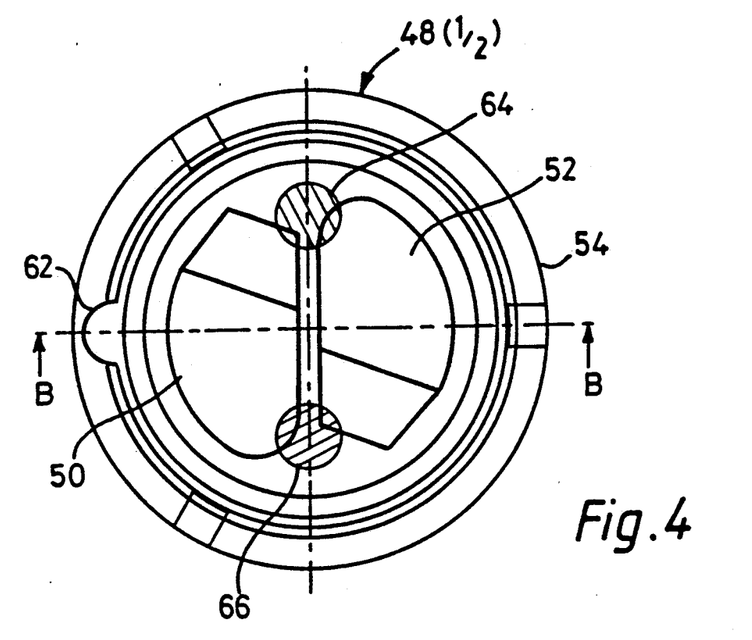
FIG. 4 is a plan view of the base of the cuvette.
Figure 5:
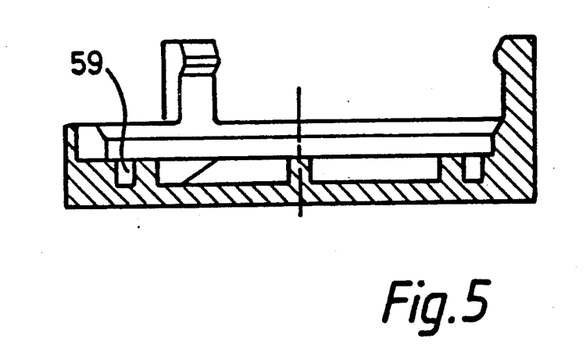
FIG. 5 is a section of the line BB of FIG. 4.

In FIG. 1 of the drawings, collimated light 10 from a source 12 is directed towards on face 14 of a cuvette generally designated 16. The face 14 includes thereon a grating or a light transmitting hologram having a refractive property similar to a convex lens, as denoted at 18, and contains spherical particles in suspension each of which is coated with a specific binding agent.

If a sample reagent containing a specific binding partner to the specific agent on the surface of the spheres is added to the cuvette 14, the diameter of the spheres increases and this results in a different light scatter pattern from the cuvette than is the case if the spheres remain at their first diameter.

A larger area photodetector or array of photodetectors or television camera of the like is located at 20 and the light scatter pattern is determined by interrogating the detectors or scanning the television camera target and the signal analysed. The circuit means for achieving the analysis is shown at 22.

A lens located to the rear of the cuvette 16 focusses any light which has been transmitted through the cuvette without being scattered, to a point at 26 at which it can be conveyed away or blocked so that it forms no part of the image on the detector 20. Light which has been scattered from one of more of the spheres will be collected by the lens and the light scatter pattern is formed on the large area detector.

The function of the lens 18 on the front wall 14 of the cuvette 16 is to divert some of the light incident on the cuvette to an off-axis point 28 at which a second photocell 30 is located. The electrical signals (if any) from the photocell 30 are supplied to a detector circuit 32 which normally transmits an inhibit signal to the remainder of the apparatus but in the presence of an electrical signal indicating that light has been received by the photocell 30 the circuit means 32 generates an enable signal to thereby enable the remainder of the apparatus to perform an assay.

In particular the inhibit signal and enable signals are applied to the circuit means 22.

The cuvette 16 is mounted so as to be rotated by an electric motor 34 through the intermediatry of a rubber drive wheel 35. Drive for the motor is effected automatically from operation of the state button switch 38 associated with control circuit 36. Appropriate interlocks and proximity switching means is provided so that circuit 36 is only enabled after a cuvette has been satisfactorily positioned within the holder (not shown). Thereafter depressing button switch 38 will cause the motor 34 to rotate and thereby rotate the holder (not showsn) through 360°. Simultaneously the control circuit 36 provides power to the light source 12 and further enables the circuit 32 for the duration of the 360° rotation.

In the event that a cuvette having a holographic lens 18 has been inserted within the carrier, and the cuvette has been located the correct way round, the holographic lens 18 will produce a spot of light which will intercept the detector 30 at some point during the rotation of the cuvette and produce a signal in the output of the detector 30 which will remove the inhibit signal in the output circuit means 32 and replace it with an enable signal. The latter then enables circuit 22. (and if If it is necessary to manually add the test sample this may now be added and the enabling signal man also enable visible or audible indicator means to indicate to the user that the sample reagent can now be added to the cuvette. The addition may be by means of a hypodermic syringe. Alternatively the sample addition may be automatic, from a reservoir or injector associated with the apparatus (not shown), or may occur as a result of shaking or rotating the cuvette.

In place of the larger area detector 20, two detectors may be located in a plane perpendicular to the axis 40. Two such detectors are shown at 42 and 44. By moving the two detectors 42 and 44 along the axis 40 towards and away from the cuvette, so the light scatter pattern intensity can be determined by summing the outputs from the two detectors 42 and 44. The technique works provided there is circular symmetry to the light scatter pattern. Such symmetry may be achieved by rotating the cuvette during the assay.

The cuvette 48 shown in FIGS. 2 to 5 is a two chamber device containing test latex in one chamber 50 and control latex in a separate chamber 52.

The cuvette includes a base 54 and a cap 56. The cap contains two ski-slope pockets (one of which is shown at 58) which contain the dried latex and which prevent its wetting until the cuvette is inverted. The chamber shape and size can help control the size of the mixing bubble and allow it to move smoothly around the chamber. A drainage groove is provided at 59.

A location feature 60 is provided on the cap and a similar feature 62 is provided on the base to control the relative orientation of cap and base $\pm/-6°$. This allows a minimum vent area of 0.2 mm$^2$ during closure of the cuvette. This prevents aerosol formation and the vent is closed once assembly of the cap and base has been completed.

Visual guide features may be added to the location feature, to make it easier to orientate by eye.

Two 4 mm diameter gratings are provided at 64 and 66 and positioned on the external face, concentrically with two 4 mm diameter viewing windows, one of which is shown at 68. The grating over the 'control' chamber 52 is orientated radially whilst that over the "reaction" chamber 50 is orientated tangentially, thus allowing the instrument to distinguish between light from the "control" and "reaction" chambers.

The gratings typically have a nominal groove spacing of 2.33 u which produce a deflection angle of 25°. The optimum 0.25 u nominal grating depth gives a nominal design diffraction efficiency for the grating of 14% at 940 mm.

There may be loss of diffraction efficiency with moulded gratings but diffraction efficiencies of greater than approximately 5% have been found to give acceptable grating signals from an agglutinating sample in the instrument.

To achieve acceptable bubble mobility cuvettes may be plasma etched in bathces, and may be treated with oxygen plasma for a period of time (typically 3 minutes) per batch.

Figure 6:
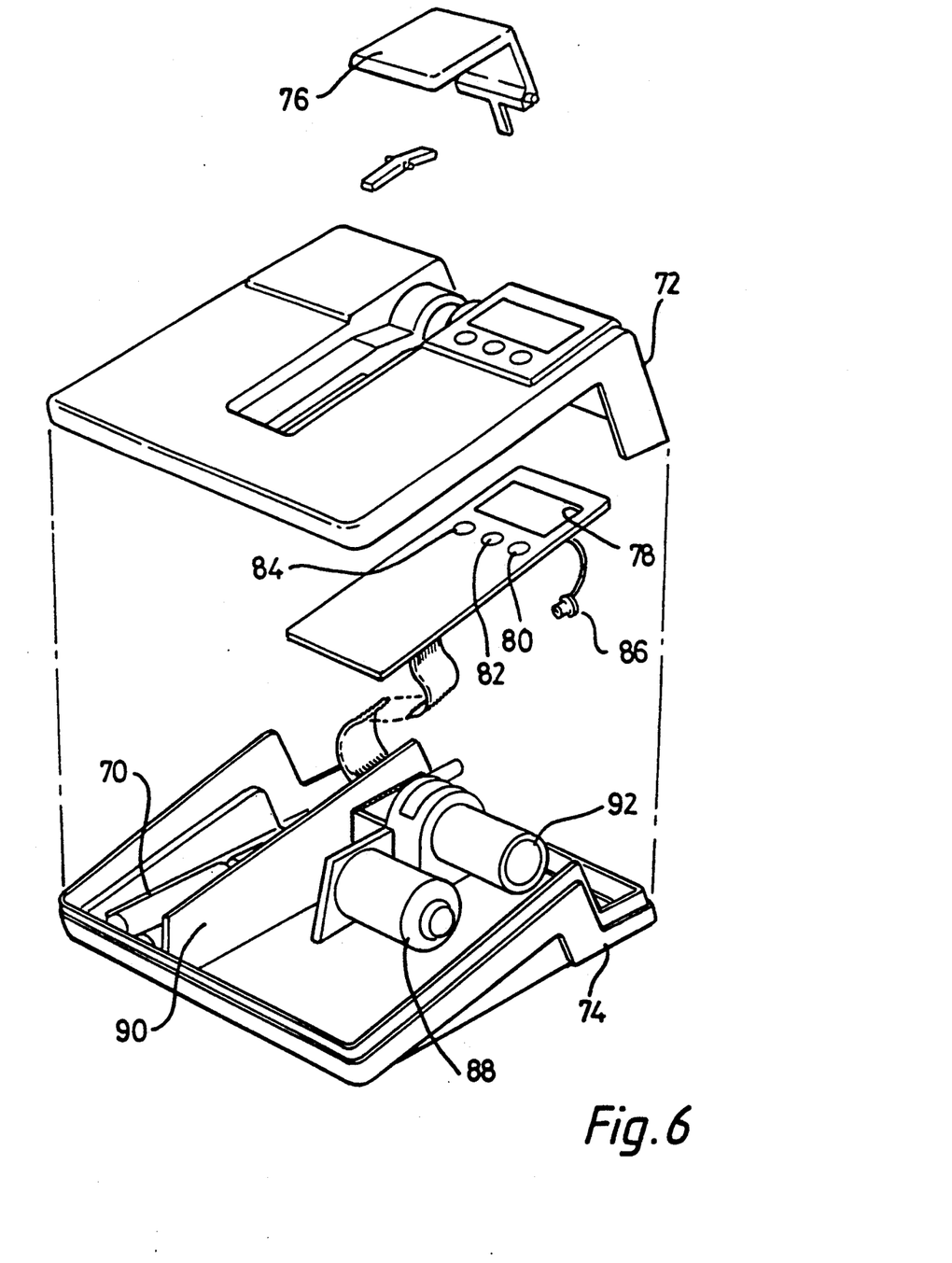
FIG. 6 is a schematic outline of a test instrument for receiving cuvettes of the type shown in FIGS. 2-5.

As shown in FIG. 6 the instrument is a small desk-top unit formed from a two-part moulding 72, 74. An opening with a light tight lid 76 accepts cuvettes for analysis. A liquid crystal display unit 78 is used to convey information to the operator, such as; pass/fail/test again/-dilute/battery low, cuvette jammed, etc. Three buttons 80, 82, 84 placed immediately below the display are used to control operation of the instrument. The unit is powered from internal cells 70 recharged from an external low voltage transformer.

The three buttons 80, 82, 84 arranged under the display, allow selection of algorithm and control the operation of the instrument.

One of the buttons 80 applies power to the unit. It is a toggle action switch, ie. push on and push off. This button is also used to abort a test.

Button 82 is used to scroll the algorithm number in the display. The selected algorithm will then be used to test data from the cuvette for pass/fail.

Button 84 is used to scroll button and is used in the same way as the button 82, to reduce the algorithm number.

The unit is turned on by pushing on/off switch 80. When power is applied the display will show the following:

algorithmn 1 if the battery power if low the battery symbol is displayed all other displays will be invisible To conduct a test the user performs the following sequence:

the test unit is switched on by pressing switch 80;

the operator first adds the sample material to the cuvette chambers 50 and 52 containing both test and control latex;

the lid 70 over the cuvette opening is opened;

the up scroll and down scroll buttons 82, 84 are pressed until the display shows the correct algorithm number for that reagent kit. The selected algorithm number will appear on a display;

the cuvette is sealed and placed into the instrument and the lid closed. The action of closing the lid causes the instrument to start operation, i.e. apply power to the LED 86 and motor 88 and enable the data collection system;

an internal timer and microprocessor controls the measurement sequence, and at the end of the measurement time, (as dicated by the algorithm number), the display will indicate Pass/Fail or Retest —(meaning test again). During the test the display shows a countdown sequence to indicate progress of the test.

the system is turned off by pushing the on/off switch 80 again. The display will then blank. All internal data is lost on turn-off.

When an estimated 10 minutes of battery life is left, the battery symbol will become visible.

The instrument uses optical diffraction to measure the rate of agglutination. A collimated beam of light falling on the latex spheres in suspension in the cuvette will cause some of the light to be diffracted from the main collimated beam. As the agglutination occurs then the effective sphere diameter increases, causing the angular distribution and the intensity of scattered light to be reduced. Circuits within the test instrument compare the rate of change of the scattered light from the test chamber and the control chamber to provide the assessment.

A simple silicon photodiode is mounted on a p.c.b. 90 and is used to monitor the intensity of scattered light. This phototide is placed at 3.5 mm from the optical axis of the system. This has been shown to provide the optimum, sensitivity. The detector used is a 1 mm$^2$ detector.

The grating detectors are similar photodivides placed apprximately 11 mm from the optical axis. These detectors are designed to sense the diffracted portion of the collimated beam from the gratings. Two detectors are used, one at top-dead centre and the other at 90°. One detector is triggered by the grating for the test chamber, and the other by the grating for the control chamber.

Two lenses are used, although not shown in FIG. 6. A collimating lens and an aperture is used to provide a collimated beam from the LED source to interrogate the cuvette. A second lens is used to collect the scattered light. The two lenses are 25 mm focal length and are of moulded plastic. The effect of the focusing lens on the diffracted beam from the grating is to create a spot 2.5×1 mm at the grating detector plane.

The cuvette has to be rotated within the instrument to allow mixing of the sample and latex material. By synchronising the measurements with the rotation a single optical system can be used to examine both test and control chambers.

A six volt DC motor 88 and gear box 92 provides the necessary rotational drive.

A magnetic coupling (not shown) is used to transmit the drive to the drive wheel within the rotation assembly which can be removed for ease of cleaning in the event of spillage of bioactive materials.

The rotation rate of the cuvette is of the order of 15 rpm.

Figure 7:
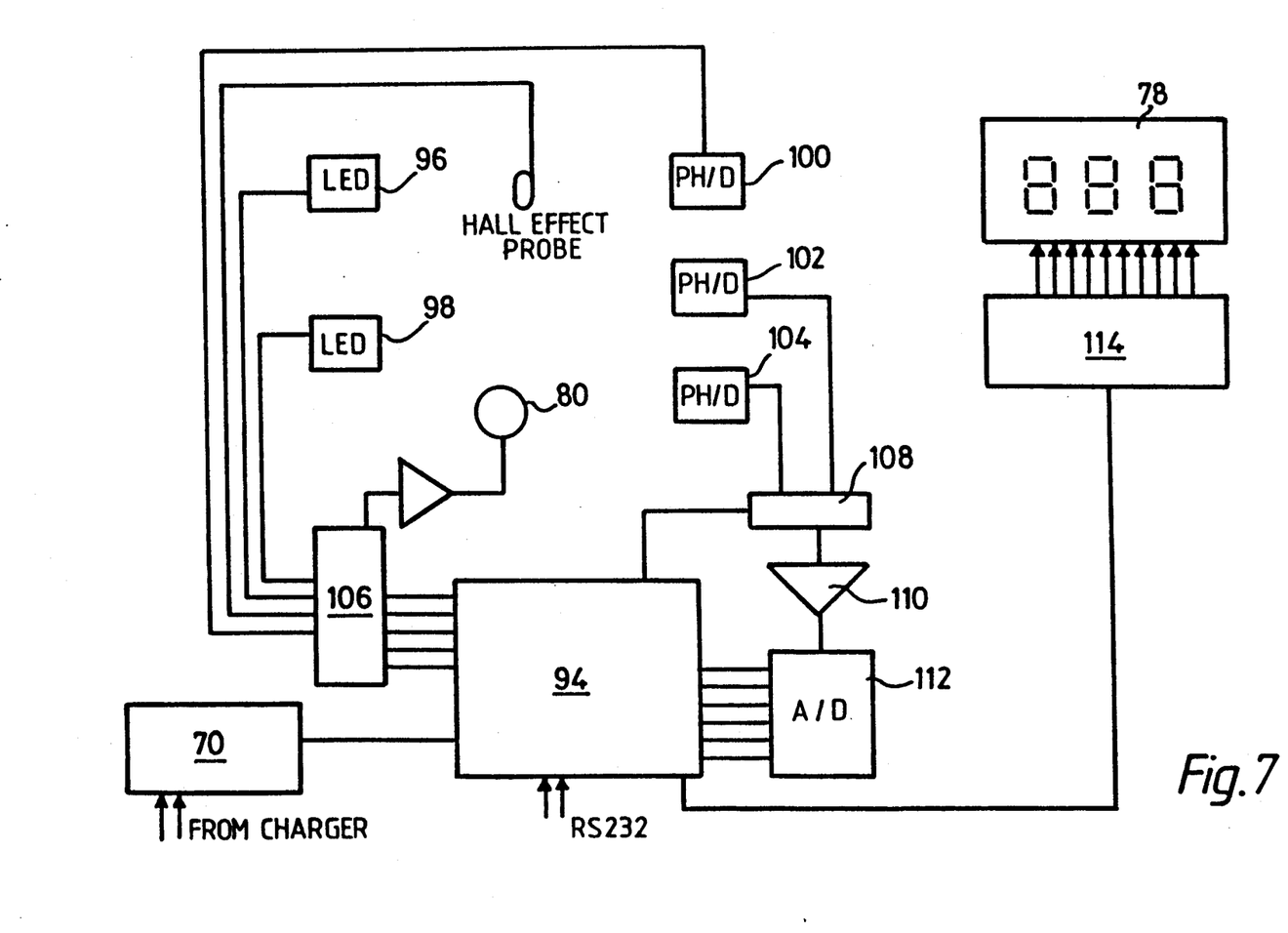
FIG. 7 is a schematic circuit diagram of the instrument of FIG. 6.

The electrical control and measuring and display circuits of the test unit are shown schematically in FIG. 7.

For convenience a single chip computer 94 manages the following functions:

reading the buttons 80, 82, 84;

providing the control data for the LCD indicator 78;

controlling the motor 88;

controlling the security LED 96 and measurement light source LED 98;

reading the security photodiode 100 and grating photodiodes 102, 104;

computing a value according to an algorithm stored in EPROM (within 94) and thereby generating a pass/fail condition based on the measured data.

A test is intiated by closing the lid 76 at which point LED, drivers 106 are switched on. Current requirements of LED are relatively high, and power can be conserved by only turning the LEDs on during measurements. The drivers 106 operate so as to provide constant current to the LEDs to ensure contant light output.

The outputs from the grating photodiodes 102, 104 are buffered and compare with a threshold voltage in selector 108 to provide a clock signal to the processing unit 94. The presence of the clock signal indicates that the appropriate chamber is in the optical beam and that a reading from the signal diode will be valid. The signals are amplified by amplifier 110 and the amplified signals are digitised by A/D converter 112 and presented to the processor unit 94 for analysis.

A display driver 114 controls the display of digits in the display unit 78, so as to provide information to the operator on the instrument status and battery condition as well as the algorithm selected and the test result.

The motor 80 is only activated when a test is in progress so as to conserve battery life, and a constant current for the motor is obtained from drives 106 and PWR amplifier 116 to maintain a constant motor speed.

The batteries are charged by an external low voltage charging unit (not shown).

Where it is necessary to provide for the instrument to be interfaced to a computer, an RS 232 interface is provided. The data to be transmitted through the RS 232 link may contain information on the time that a sample was measured, and the voltage level of that sample.

The decision on whether a particular sample has passed or failed a test will be made by measuring the rate of change of the signal falling on the signal photodiode, since this gradient appears to be a good indicator of infection.

The casing parts 72, 74 may be from injection moulded plastics. The lid 76 may be light tight. The space occupied by the cuvette and magnetically coupled drive wheel must be capable of being cleaned by flushing with alcohol or other sterilising agents. A feature of the lid mechanism is that it is preferred that when the lid is opened the cuvette will be ejected into an exit channel. This will allow the next cuvette to be loaded before final removal of the last cuvette.

Reagent types which can be used with the instrument can be found in the Orion Diagnostica's range of reagent kits, i.e. Rotalex, Adenalex, Hemolex, Rubalex, Respiralex, and Myolex.

A number of algorithms sufficient to satisfy Orion Diagnostica's range of test kints are stored in a PROM section of the processor 94.

We claim:

1. Apparatus for performing a biological assay, comprising:
   a cuvette adapted to contain spherical particles having a binding agent on the surface thereof and which have a detectably different light scattering characteristic in the presence of a material having a specific binding partner for the binding agent on the spheres,
   means for illuminating the cuvette,
   an optical element at the wall of the cuvette for deflecting at least some of the illuminating light to an off-axis point,
   detector means at said point for detecting the deflected light, and
   circuit means responsive to a signal output of the detector means for enabling the assay to be performed only if light is present at said off-axis point.

2. An apparatus as claimed in claim 1, in combination with means for rotating the cuvette about its axis, so that the said point can lie at any position around a circular path.

3. An apparatus as claimed in claim 1, wherein the optical element is a diffraction grating.

4. A method of performing a biological assay which includes the preliminary operation of checking whether a cuvette has a specific optical element in or on the wall of said cuvette, comprising the steps of illuminating the cuvette, effecting relative rotation between the cuvette and a light sensitive, off-axis detector, investigating whether the detector generates a particular electrical signal during the rotation caused by light deflected by the optical element being incident on the detector, and substantially carrying out the biological assay only if said particular electrical signal is generated.

5. A method as claimed in claim 4, in which if no such particular electrical signal is generated, instead an inhibit signal is generated preventing further use of the cuvette.

6. Apparatus for performing a biological assay on the contents of a cuvette which contains a plurality of spheres having a specific binding agent on the surface thereof and to which a sample reagent is to be added which may or may not contain a specific binding partner for the agent on the spheres, the presence of a specific binding partner being detected by an increase in diameter of the spheres which results in a different light scatter pattern from the spheres in the presence of appropriate illumination, and which includes detector means for determining the light scatter pattern before and after a sample reagent has been added, including
   means for automatically illuminating the cuvette,
   means for moving the cuvette in a predictable manner to effect at least a preliminary movement of said cuvette,
   a light sensitive detector for checking for the presence of light at a point along a path which light will be diverted from a particular optical element located at a wall of the cuvette, and
   circuit means responsive to electrical signals from the light sensitive detector which normally inhibits the operation of the apparatus to perform the said assay but which generates an enabling signal to permit the apparatus to perform the assay if an appropriate signal pulse is generated by the detector during the said preliminary movement of the cuvette.

7. Apparatus as claimed in claim 6, which said means for moving rotates the cuvette, and further including circuit means to determine the number of signal pulses generated during a single rotation and to determine that a cuvette is identified as being acceptable if only one signal pulse is generated during the rotation of the cuvette.

8. Apparatus as claimed in claim 6, which includes automated sample reagent addition means and means to inhibit the addition means until the apparatus has verified by generation of the enabling signal that the cuvette incorporates the particular optical element.

9. Apparatus as claimed in claim 6, in which said path includes lenses which co-operate, in the presence of the particular optical element at the wall of the cuvette, to focus light diverted by the optical element onto the light sensitive detector.

10. Apparatus as claimed in claim 6, in which the cuvette has a central axis about which said cuvette is rotated and drive means is provided for rotating the cuvette.

11. An analyser for use with a cuvette which includes an optical element as at least part of one of its walls to divert light incident thereon off axis in a particular direction, and by which a biological assay can be performed by investigating the change in light scatter from coated spheres within the cuvette due to chemical bonding with the cuvette, including
   (a) a source of light for projecting light onto a wall of the cuvette having the optical element formed therein,
   (b) first light detector means from which electrical signals can be obtained for determining changes in the pattern of the light scattered by particles contained within the cuvette, due to the addition of a sample reagent thereto,
   (c) second light detector means radially displaced from the axis for receiving light diverted by an optical element in the cuvette, and
   (d) circuit means responsive to the second detection means for inhibiting performance of the biological assay if said second detector means does not receive diverted light.

12. An analyser as claimed in claim 11 in which the first light detector means comprises a pair of detectors, spaced apart, which are movable relative to the cuvette to provide two electrical signals which can be combined to enable the slope of the light scatter patter to be derived by computing the mean value of the two electrical signals so obtained.

13. An analyser as claimed in claim 11, in which the light employed to illuminate the cuvette is collimated.

14. A method of performing a biological assay comprising the steps of:
   (a) inserting a cuvette into an analyser;
   (b) shining light through the cuvette so as to at least in part divert the light by an optical element in the cuvette;
   (c) rotating the cuvette relative to a light detector situated on a circular path which the said diverted light will describe as the cuvette is rotated to generate an electrical signal output when light falls on the detector during the said rotation;
   (d) determining if a single electrical pulse appears in the output of the detector during the rotation of the cuvette about its axis and generating an enabling signal for the analyser if a single electrical pulse appears;

(e) causing a mixing of the sample reagent and the coated spheres in the cuvette, and
(f) performing the assay by comparing light scatter before and after mixing, only if the enabling signal is generated.

* * * * *